US007427694B2

(12) United States Patent
Blaschke et al.

(10) Patent No.: US 7,427,694 B2
(45) Date of Patent: Sep. 23, 2008

(54) PROCESS FOR THE PREPARATION OF HIGH-PURITY BISPHENOL A

(75) Inventors: Ulrich Blaschke, Krefeld (DE); Stefan Westernacher, Kempen (DE); Arne Braun, Leverkusen (DE); Raymond Audenaert, Hamme (BE); Jesko Zank, Köln (DE)

(73) Assignee: Bayer Materialscience AG, Leverkusen (DE)

( * ) Notice: Subject to any disclaimer, the term of this patent is extended or adjusted under 35 U.S.C. 154(b) by 0 days.

(21) Appl. No.: 11/971,314

(22) Filed: Jan. 9, 2008

(65) Prior Publication Data

US 2008/0108851 A1 May 8, 2008

Related U.S. Application Data

(63) Continuation of application No. 11/446,368, filed on Jun. 5, 2006.

(30) Foreign Application Priority Data

Jun. 4, 2005 (DE) .................. 10 2005 025 788

(51) Int. Cl.
*C07C 37/68* (2006.01)
(52) U.S. Cl. ..................................... 568/724
(58) Field of Classification Search .................. 568/724
See application file for complete search history.

(56) References Cited

U.S. PATENT DOCUMENTS

| 2,775,620 | A | 12/1956 | Williamson |
|---|---|---|---|
| 5,198,591 | A | 3/1993 | Kiedik et al. |
| 5,243,093 | A | 9/1993 | Kissinger et al. |
| 5,315,042 | A | 5/1994 | Cipullo et al. |
| 6,384,288 | B1 | 5/2002 | Kuhling et al. |
| 6,686,508 | B2 | 2/2004 | Hirano et al. |
| 6,706,848 | B1 | 3/2004 | Prein et al. |
| 6,710,211 | B1 | 3/2004 | Heydenreich et al. |
| 6,906,227 | B2 | 6/2005 | Neumann et al. |
| 6,919,487 | B2 | 7/2005 | Neumann et al. |
| 2002/0183562 | A1 | 12/2002 | Neumann et al. |
| 2003/0038094 | A1 | 2/2003 | Neumann et al. |
| 2003/0120120 | A1 | 6/2003 | Hirano et al. |
| 2003/0181768 | A1 | 9/2003 | O'Young et al. |
| 2005/0222467 | A1 | 10/2005 | Kodama et al. |

FOREIGN PATENT DOCUMENTS

| DE | 19848026 | 4/2000 |
|---|---|---|
| DE | 19954787 | 5/2001 |
| DE | 19960144 | 6/2001 |
| DE | 19961521 | 6/2001 |
| DE | 19961566 | 6/2001 |
| EP | 0718267 | 6/1996 |
| EP | 0718268 | 6/1996 |
| EP | 1367043 | 12/2003 |
| PL | 159620 B | 12/1992 |
| WO | WO 00/35847 | 6/2000 |
| WO | WO 02/40435 | 5/2002 |
| WO | WO 03/082785 | 10/2003 |

*Primary Examiner*—Yvonne Eyler
*Assistant Examiner*—Kellette Gale
(74) *Attorney, Agent, or Firm*—Womble Carlyle Sandridge & Rice, PLLC

(57) ABSTRACT

A process for the preparation of high purity bisphenol A is disclosed. The multi-step process entails a process whereby bisphenol A of a purity of preferably at least 99.8% can be obtained.

14 Claims, No Drawings

PROCESS FOR THE PREPARATION OF HIGH-PURITY BISPHENOL A

CROSS REFERENCE TO RELATED APPLICATIONS

This application is a continuation of U.S. application Ser. No. 11/446,368 filed Jun. 5, 2006 which claims priority to German Application No. 1020050257887 filed Jun. 4, 2005, the content of which is incorporated herein by reference in its entirety.

BACKGROUND OF THE INVENTION

1. Field of the Invention

The invention relates to a process and in particular to a process for preparing bisphenol A.

2. Description of Related Art 2,2-Bis(4-hydroxyphenyl)propane (bisphenol A, BPA), which is the condensation product of phenol and acetone, is a starting material or intermediate for the preparation of a large number of commercial products. Thus it is used as a starting material for the preparation of various types of polymeric materials, for example polyarylates, polyetherimides, polysulfones and modified phenol-formaldehyde resins. Preferred fields of application are in the preparation of epoxy resins and polycarbonates.

Technically relevant methods of preparing BPA are known, e.g. WO 00/35847 and U.S. Pat. No. 2,775,620.

After the acid-catalyzed reaction of phenol with acetone, BPA is separated from the product mixture in the form of a crystalline adduct of BPA and phenol. Phenol is completely or partially removed from these crystals of BPA-phenol adduct by distillative, desorptive or extractive methods. Before the separation from phenol, the crystals of BPA-phenol adduct may also be subjected to additional purification steps to reduce the concentration of secondary components.

The crystals of BPA-phenol adduct may be recrystallized e.g. from phenol, organic solvents or mixtures of these solvents. The phenol present in the adduct crystals may also be completely or partially separated off using an appropriate solvent.

PL 159620 describes a laborious process for the purification of bisphenol A wherein the crystals of BPA-phenol adduct isolated in a first stage are dissolved in phenol and the resulting solution is cooled in a batch crystallizer in a system similar to a static multilayer crystallization process, wherein crystals of BPA-phenol adduct growing on the tubes. When the mother liquor has been drained off, the crystals of BPA-phenol adduct recrystallized in this way are washed with phenol and water in order to remove any mother liquor still adhering to crystals. Alternatively, or in addition, the crystals can be purified further by heating to a temperature of 75 to 85° C., i.e. by exudation. However, as the process has to be carried out batchwise, equipment costs are typically high. Moreover, the production outputs based on the heat-transfer area are an order of magnitude lower in a process according to PL '620 than in a continuous suspension crystallization process used to produce crystals of BPA-phenol adduct. Furthermore, an acceptable space-time yield requires high cooling rates, so a multilayer crystallization of this type has to take place at substantially higher crystal growth rates than a continuous suspension crystallization. The resultant increased incorporation of impurities into the crystals has to be compensated by time-intensive exudation and/or washing operations. If a high purity is required, it may be necessary to use a multistage process.

EP 718 268 A describes a process for the preparation of a crystalline adduct of bisphenol A and phenol wherein BPA dissolved in phenol is first crystallized out as an adduct and filtered off. It is then redissolved in phenol, crystallized out again and filtered off, and the step of recrystallization being repeated several times. In the last step of the multistage recrystallization, the adduct is washed with specially purified phenol. The washing liquids and filtrates for washing and dissolving the adducts are at least partially recycled.

WO 02/40435 describes a process wherein high-purity bisphenol A is obtained by multiple recrystallization from phenol and washing of the adducts in individual stages with high-purity phenol in a cross-flow washing plant. The phenol used as washing phenol contains virtually no bisphenol A or isomers thereof. A multiple recrystallization is preferred. Washing with high-purity phenol at each of the individual stages requires a very large amount of high-purity phenol. Furthermore, a large amount of bisphenol A is dissolved in the phenol at each individual stage, resulting in losses of yield.

WO 03/82785 describes a process for the preparation of bisphenol A wherein in the first step a suspension of crystals of BPA-phenol adduct is filtered under vacuum and washed, and the resulting filter cake is dissolved in a liquid containing phenol and crystallized again. The crystals obtained are separated off by centrifugation. However, the continuous (filter) centrifuges that are more economical for larger plant capacities demand a minimum crystal size, which requires special crystallization procedures.

EP 1 367 043 A describes a process for the purification of bisphenol A wherein the crystals of BPA-phenol adduct are dissolved in phenol and the resulting solution is filtered at least once before the crystals of BPA-phenol adduct are crystallized out again.

SUMMARY OF THE INVENTION

A process for the preparation of high purity bisphenol A is disclosed. The multi-step process entails a) reacting phenol with acetone in the presence of an acidic ion exchanger and a sulfur-containing co-catalyst to give a product mixture that includes bisphenol A and phenol; b) continuously obtaining from the product mixture crystals of bisphenol A-phenol adduct by suspension crystallization, c) separating the adduct obtained in step (b) by solid-liquid separation to obtain a solid phase and a liquid phase d) washing of the solid phase with a solution containing phenol to obtain washed solid phase and a second liquid phase, e) distilling the liquid phase and said second liquid phase to obtain dewatered solution containing 5 to 15% p,p-BPA, 3 to 12% isomers of BPA and less than 0.3% water, f) introducing of at least 90% by weight of the dewatered solution into step (a), g) adding phenol to the washed solid phase obtained in step d) to obtain a homogeneous material system that contains p,p'-BPA, isomers of BPA and water h) continuously obtaining from the homogeneous material system crystals of bisphenol A-phenol adduct by suspension crystallization; i) separating the crystals obtained in step (h) by solid-liquid separation to obtain a second solid phase, j) washing the second solid phase with a solution that contains phenol to obtain a washed adduct; and k) heating the washed adduct to remove phenol.

Additional objects, features and advantages of the invention will be set forth in the description which follows, and in part, will be obvious from the description, or may be learned by practice of the invention. The objects, features and advantages of the invention may be realized and obtained by means of the instrumentalities and combination particularly pointed out in the appended claims.

DETAILED DESCRIPTION OF A PREFERRED EMBODIMENT

An object of the present invention was to provide a simple process for the preparation of high-purity bisphenol, especially bisphenol A, with a purity of preferably at least 99.8%, to give a low color index and a high temperature stability in the melt.

A low color index is understood as meaning a color index of at most 20 Hazen units. To determine the color index, 10 g of bisphenol A are melted under air in an oil bath at a temperature of 175° C. over 20 minutes, after which the color index is determined immediately according to ASTM D 1209. To determine the temperature stability, this material is then heated for 4.5 h at a bath temperature of 175° C., after which the color index is measured again. A high temperature stability is understood as meaning that the color index increases by at most 40 Hazen units.

The invention provides a process for the preparation of bisphenol A advantageously comprising the following steps:
 a) reacting phenol with acetone in the presence of an acidic ion exchanger and a sulfur-containing co-catalyst to give a product mixture that includes bisphenol A, phenol, BPA isomers, un-reacted acetone, and water,
 b) continuously obtaining from the product mixture crystals of bisphenol A-phenol adduct by suspension crystallization in at least one crystallizer equipped with at least one heat exchanger, said product mixture containing 0.1 to 6% by weight of water,
 c) separating the adduct obtained in step (b) by solid-liquid separation to obtain a first solid phase and a first liquid phase,
 d) washing of the first solid phase with a solution containing phenol to obtain a washed solid phase and a second liquid phase,
 e) distilling the first liquid phase and said second liquid phase to obtain dewatered solution comprising 5 to 15 wt.-% p,p-BPA, 3 to 12 wt.-% isomers of BPA and less than 0.3 wt.-% water, the percentages based on the weight of the dewatered solution,
 f) optionally introducing of at least 90 wt.-% by weight of the dewatered solution into step (a),
 g) adding phenol to the washed solid phase obtained in step d) to obtain a homogeneous material system comprising 15 to 35 wt.-% p,p'-BPA, 0.05 to 2 wt.-% isomers of BPA and 0.1 to 10 wt.-% water,
 h) continuously obtaining from the homogeneous material system crystals of bisphenol A-phenol adduct by suspension crystallization in at least one crystallizer equipped with at least one heat exchanger,
 i) separating the crystals obtained in step (h) by solid-liquid separation to obtain a second solid phase,
 j) washing the second solid phase with a solution that contains phenol to obtain a washed adduct, and
 k) heating the washed adduct to at least 120° C. to remove phenol.

According to a further embodiment, there is provided a process for the preparation of bisphenol A comprising:
 a) reacting phenol with acetone in the presence of an acidic ion exchanger and a sulfur-containing co-catalyst to produce a product mixture comprising bisphenol A, phenol, BPA isomers, un-reacted acetone, and water;
 b) continuously obtaining from the product mixture crystals of bisphenol A-phenol adduct by suspension crystallization in at least one crystallizer provided with at least one heat exchanger, said product mixture containing 0.1 to 6% by weight of water,
 c) separating the adduct obtained in (b) by a first solid-liquid separation to obtain a first solid phase and a first liquid phase,
 d) washing the first solid phase with a solution comprising phenol to obtain a washed solid phase and a second liquid phase,
 e) distilling the first liquid phase and said second liquid phase to obtain a dewatered solution of BPA and isomers thereof, preferably 5 to 15 wt.-% p,p-BPA, 3 to 12 wt.% isomers of BPA and less than about 0.3 wt.-% water, the percentages based on the weight of the dewatered solution,
 f) optionally introducing at least a portion of, or at least 90 wt.-% by weight of the dewatered solution into (a),
 g) adding phenol to the washed solid phase obtained in (d) to obtain a homogeneous material system comprising 15 to 35 wt.-% p,p'-BPA, 0.05 to 2 wt.-% isomers of BPA and 0.1 to 10 wt.-% water,
 h) continuously obtaining from the homogeneous material system crystals of bisphenol A-phenol adduct by suspension crystallization in at least one crystallizer provided with at least one heat exchanger,
 i) separating the crystals obtained in (h) by a second solid-liquid separation to obtain a second solid phase,
 j) washing the second solid phase with a solution comprising phenol to obtain a washed adduct, and
 k) optionally heating the washed adduct to at least 120° C. to at least potentially or partially remove phenol.

A process according to the present invention affords a bisphenol A with a purity of preferably at least 99.8 wt-% of p,p-BPA, based on all the components contained in the product, except phenol.

In step (a) of a process according to the invention, the reaction of phenol and acetone advantageously takes place in the presence of an acidic ion exchanger and a sulfur-containing co-catalyst to give a product mixture containing bisphenol A. Step (a) is based on the acid-catalyzed reaction of phenol with acetone, and the phenol/acetone ratio in the reaction is preferably adjusted to at least 5:1. The reaction is conventionally carried out continuously and generally at temperatures from 45 to 110° C., preferably from 50 to 80° C. Acidic catalysts used are suitably gel-like (microporous) or macroporous sulfonated crosslinked polystyrene resins (acidic ion exchangers), which may be either monodisperse or heterodisperse as desired. Divinylbenzene is normally used as the crosslinking agent, but other crosslinking agents, such as divinylbiphenyl, may also be used if desired for any reason. The catalyst is advantageously used together with a co-catalyst, which conventionally is a thiol carrying at least one SH group and having a positive influence on both the selectivity and the reactivity of the reaction. The co-catalyst may be in any form, such as homogeneously dissolved in the reaction solution or fixed to the catalyst itself. Examples of suitable homogeneous co-catalysts include mercaptopropionic acid, hydrogen sulfide, alkyl sulfides or alkylsilylthiols, such as ethyl sulfide or silylmethanethiol and similar compounds. Fixed co-catalysts include aminoalkylthiols and pyridylalkylthiols ionically bonded to the catalyst, it being possible for the SH group to be protected and to be freed only during or after fixation to the catalyst, e.g. as in the case of dimethylthiazolidine and alkylcarbamoylalkylthio esters. The co-catalyst may also be covalently bonded to the catalyst as an alkylthiol or arylthiol, or be a constituent of the catalyst. It is also possible for two or more co-catalysts to be used together.

Apart from unreacted phenol and optionally acetone, the product mixture formed in the reaction of phenol with acetone in the presence of acidic catalysts preferably contains essentially BPA and water. These are accompanied by small amounts of isomers as typical by-products of the condensation reaction, examples being 2-(4-hydroxyphenyl)-2-(2-hydroxyphenyl)propane (o,p-BPA), substituted indanes, hydroxyphenylindanols, hydroxyphenylchromans, spiro-bisindanes, substituted indenols, substituted xanthenes and more highly condensed compounds having three or more phenyl rings in the molecular skeleton. Other secondary components, such as anisole, mesityl oxide, mesitylene and diacetone alcohol, may also form due to autocondensation of the acetone and reaction with impurities in the raw materials.

The reaction in step (a) may advantageously be carried out in such a way that the acetone is completely converted. For economic and technical reasons, however, it is usually carried out so that, rather than 100% of the acetone being converted, up to 1.0 wt-% of acetone still remains in the reactor outflow.

If desired, the reaction may also take place in several reactors connected in series. The total amount of acetone is preferably distributed so that acetone is metered in before the reaction mixture enters each reactor.

By-products, as well as the unreacted starting materials such as phenol and acetone, can detract from the suitability of BPA in some cases for the preparation of polymers and have to be separated off by suitable processes because high purity demands are made on the BPA, especially for the preparation of polycarbonate.

From the product mixture obtained in step (a), which contains 0.1 to 6 wt-% and preferably 0.5 to 2 wt-% of water, crystals of bisphenol A-phenol adduct are crystallized out in step (b) by continuous suspension crystallization. The product mixture obtained in step (a) is not subjected to distillation upstream of step (b) or (c) to remove readily volatile constituents (including water).

The crystallization may take place in one or more crystallizers connected in series. Any crystallizer known to those of skill in the art can advantageously be used as well as any devise that can achieve the desired crystallization to produce bisphenol A. The mean total residence time of the crystals in this crystallization stage is preferably 30 minutes to ten hours. With a correspondingly slow crystallization, the inclusion of mother liquor and the incorporation of impurities into the crystals of BPA-phenol adduct may be avoided to a large extent. Cooling can be effected indirectly if desired such as by using at least one heat exchanger. In the crystallization, the product mixture can be cooled to 40 to 50° C. in one crystallization step. Preferably, however, the crystallization takes place in two steps, the product mixture being cooled to a temperature of 50 to 65° C. in a first step and then to a temperature of 40 to 50° C. in a second step. In both embodiments, the cooling can be effected by using one or more heat exchangers per crystallizer.

In one preferred embodiment, the temperature of the product mixture can be adjusted upstream of step (b) to a temperature that is preferably at most 5° C. above the crystallization point of the mixture.

Any subsequent solid-liquid separation, especially filtration in step (c), and washing in step (d) may be carried out e.g. in or on one of the following representative types of apparatus: continuous filter centrifuges such as screen-conveyor centrifuges or pusher centrifuges, batch filter centrifuges such as skimmer centrifuges, and continuous filters such as rotary or drum filters, belt filters and disk filters. It may be preferable in some cases to use rotary filters, and particularly vacuum rotary filters.

In the case of filtration using a vacuum rotary filter, filtration is preferably carried out as described in DE 199 61 521 A, the content of which is incorporated herein by reference.

The washing of the solid phase, especially the filter cake, can be effected by employing a phenolic solution, which extensively displaces the mother liquor remaining in the filter cake and frees the crystals of BPA-phenol adduct from impurities adhering to the surface thereof. The filter cake may be washed with a single phenolic solution or several phenolic solutions of different compositions, which can suitably be applied successively or as a mixture, e.g. via spray nozzles. Averaged over the total amount used, the phenolic solution preferably contains 84 to 99.45 wt-% of phenol, 0.5 to 15 wt-% of BPA and 0.05 to 1.1 wt-% of isomers. These concentrations are based on the total weight of the phenolic solution without water. The phenolic solution used preferably contains 0.05 to 12 wt-% water, preferably 0.2 to 3 wt-% of water, based on the total amount (of phenolic solution), and 5 to 100 wt-% thereof preferably originates from step (i) and/or (j). The temperature of the washing liquid is preferably from 40 to 85° C., and particularly preferably from 45 to 70° C. In the case of a rotary filter, part of the phenolic solution from step (i) and/or (j) may be used for rinsing the rotary filter in step (c) and (d), or any part thereof such as a cloth.

The adduct crystals obtained in step (d) can be present in the form of a filter cake moistened with phenol, and in this case preferably have a BPA purity of at least 99 wt-%, based on the sum of BPA and all other components. The residual moisture in the filter cake as a proportion by weight of the liquid adhering to the crystals of BPA-phenol adduct, based on the total weight of moist filter cake, is preferably below 40 wt-% and more preferably 15 to 30 wt-%. Preferably, the amount of phenolic solution for washing the filtered crystals of bisphenol A-phenol adduct is chosen so that the amount of washing liquid advantageously corresponds to 20 to 120 wt-% of the amount of filtered crystals of BPA-phenol adduct. The amount used is preferably 50 to 90 wt-%.

Preferably, water can be completely or partially removed by distillation from the liquid phase obtained in step (c) and (d) from the solid-liquid separation and/or the washing, especially down to a content of 0 to 0.3 wt-%, after which optionally at least 90 wt-% thereof is advantageously recycled into step (a), optionally after the addition of acetone, phenol and/or a homogeneous co-catalyst. The recycled solution contains preferably 5 to 15 wt-% and particularly preferably 6.5 to 10 wt-% p,p'-BPA and 3 to 12 wt-% isomers, obtained in step (e).

In the next step, (g), a homogeneous solution containing, inter alia, preferably 15 to 35 wt-% and particularly preferably 20 to 30 wt-% BPA and preferably 0.05 to 2 wt-% and particularly preferably 0.1 to 1.1 wt-% isomers, is prepared by adding a phenolic solution to crystals of BPA-phenol adduct obtained in step (d). This can be done by mixing the crystals of BPA-phenol adduct with a phenolic solution, the temperature of the resulting solution preferably being 70 to 100° C., and advantageously being adjusted so that the homogeneous solution is subsaturated.

In one preferred embodiment, the crystals of BPA-phenol adduct moistened with phenol from step (d) are first melted to give a homogeneous melt typically having a temperature of 90 to 140° C., and preferably of 95 to 130° C. A phenolic solution is then admixed. This procedure assures a thorough mixing and a rapid preparation of the BPA-phenol solution. It likewise avoids a situation where individual contaminated crystals from the first crystallization step do not dissolve, causing contamination of the end product.

The amount of phenolic solution used in step (g) can advantageously be adjusted so that the resulting homogeneous solution preferably has a p,p'-BPA content of 15 to 35 wt-% and more preferably of 20 to 30 wt-%. The concentration of isomers is preferably 0.05 to 2 wt-%, more preferably 0.1 to 0.8 wt-%, and particularly preferably 0.2 to 0.5 wt-%. These concentrations are based on the solution without taking the water into account.

The homogeneous solution of BPA in phenol prepared in step (g) preferably contains 0.1 to 10 wt-% of water and particularly preferably 0.2 to 3 wt-% of water. If the homogeneous solution were to contain no water, an increasing amount of acicular crystals would potentially be obtained in the next step(s) of crystallization, with the low concentrations of isomers in the mother liquor, and acicular crystals may lead to various problems in the production facility, namely, inter alia, accelerated fouling on cooling surfaces during crystallization, and deterioration of washing performance in the solid-liquid separation. This may detract from the product quality. The presence of water produces sturdy crystals, i.e. shorter and thicker crystals. Moreover, the presence of water in these concentrations during the crystallization has the effect of reducing the incorporation of impurities into the crystals, thereby allowing a further increase in product purity.

In another embodiment according to the present invention, independently of the operating temperatures in the crystallizers, it is possible to add acetone in concentrations of 0 or 0.1- to 5 wt-%, based on the resulting mixture, as a further degree of freedom other than the addition of water. This measure makes it possible, inter alia, to optimize the crystal morphology, the solid-liquid separation behavior, the fouling tendency and the behavior of impurities with respect to incorporation into the adduct crystals, and/or to adjust the concentration of the mother liquor. A continuous suspension crystallization of a BPA-phenol adduct from the homogeneous solution obtained in step (g) is then carried out in step (h). Crystals of bisphenol A-phenol adduct are obtained in step (h) by continuous suspension crystallization from the homogeneous solution obtained in step (g), and these crystals are separated from the liquid phase by solid-liquid separation (step i), especially filtration, and then washed with a phenolic solution (step (j)). The cooling in step (h) can be effected indirectly by means of heat exchangers.

The crystallization may take place in one or more crystallizers connected in series if desired. The mean total residence time of the crystals in this crystallization stage should preferably be between half an hour and ten hours. With a correspondingly slow crystallization, the inclusion of mother liquor and the incorporation of impurities into the crystals of BPA-phenol adduct may be prevented to the greatest possible extent. During crystallization, the product mixture may be cooled to 35 to 55° C. in one crystallization step, for example, it being possible for one or more crystallizers to be operated in parallel. Alternatively, the crystallization may take place in two or more steps, the product mixture being cooled to a temperature of 45 to 70° C. in a first step and then to a temperature of 35 to 55° C. in a second step. In both embodiments, the cooling can be effected using one or more heat exchangers per crystallizer.

The details of an alternative embodiment of the two crystallization stages (b) and (h) are as follows: In the first crystallization stage (step (b)) the crystallization takes place in two steps in series, and in the second stage (step (h)) it takes place in one step in one or more crystallizers operated in parallel. A step within a crystallization stage is understood as meaning a crystallization in a specific temperature range. A crystallization stage carried out in two steps in series is thus carried out in two different temperature ranges in succession. Using stepwise crystallization in the first stage achieves a greater purity. Because of the lower isomer contents present and the increased fouling tendency associated therewith, a longer working life of the heat exchangers is achieved by conducting crystallization in one step for the second stage. In one preferred embodiment, the temperature of the product mixture is adjusted upstream of step (h) to a temperature that is at most 5° C. above the crystallization point.

The subsequent solid-liquid separation step (i), especially filtration, and washing in step (j) are carried out e.g. in or on one of the following types of apparatus: continuous filter centrifuges such as screen-conveyor centrifuges or pusher centrifuges, batch filter centrifuges such as skimmer centrifuges, and/or continuous filters such as rotary or drum filters, belt filters and disk filters. It is preferable to use rotary filters and particularly vacuum rotary filters. It is particularly preferable to use a type of apparatus that can also be employed in step (c) and (d).

In the case of filtration by means of a vacuum rotary filter, the filtration is preferably carried out as described in DE 199 61 521 A, the content of which is incorporated herein by reference.

The washing of the solid phase, especially the filter cake, can be effected with a phenolic solution, which extensively displaces the mother liquor remaining in the filter cake and frees the adduct crystals from impurities adhering to the surface. The solid phase, especially the filter cake, may be washed with a single phenolic solution or several phenolic solutions, which are applied successively or as a mixture, e.g. via spray nozzles.

The phenolic solution used for washing the recrystallized crystals of BPA-phenol adduct in step (j) may be either fresh phenol, i.e. commercially available phenol, or recycled phenols obtained for the production facility, or mixtures of the two. A recycled phenol is understood as meaning a phenol that is obtained in the course of the process and recycled into the process. It is also possible to use phenols obtained in the preparation of polycarbonate by the melt process. The washing phenol used here preferably contains in total, a maximum of 1.0 wt-% of other phenolic components, e.g. isopropenylphenol, BPA and its isomers and secondary components. Recycled phenols, e.g. from the removal of phenols from the crystals of BPA-phenol adduct, are purified here only by distillation, if at all. The temperature of the washing phenol is advantageously 41 to 75° C. and preferably 45 to 60° C. The washing phenol may contain up to 10 wt-% of water.

The adduct crystals obtained in step (j) in the form of a solid phase moistened with phenol, especially a filter cake moistened with phenol, preferably have a BPA purity of at least 99.8 wt-%, based on the sum of BPA and secondary components. The residual moisture in the filter cake as a proportion by weight of the liquid adhering to the crystals of BPA-phenol adduct, based on the total weight of moist filter cake, is advantageously below 40 wt-% and preferably from 15 to 30 wt-%. Preferably, the amount of phenolic solution for washing the filtered crystals of bisphenol A-phenol adduct is chosen so that the amount of washing liquid corresponds to 20 to 120 wt-% of the amount of filtered crystals of BPA-phenol adduct. The amount used is particularly preferably 50 to 90 wt-%.

The liquid phase from (i) and (j), especially the filtrate, from the solid-liquid separation of the second crystallization stage, (i), can be used in step (g) for mixing with the molten filter cake from (d), and in step (c) for washing the filter cake and/or for rinsing purposes (e.g. washing the cloth), optionally after the addition of water and/or acetone. Preferably 10 to 50 wt-% and particularly preferably 20 to 40 wt-% of the liquid phase obtained in step (i) and/or (j) is recycled into step (d) for washing purposes. Also, preferably 50 to 90 wt-% and particularly preferably 60 to 80 wt-% of the filtrates obtained in step (i) and/or (j) are used in step (g).

In one preferred embodiment, all or part of the mother liquor obtained in step (i) and of the washing and dehumidifying filtrates (j) may be collected separately. The filtrates from washing and dehumidifying, which are less contaminated with isomers, are preferably passed to step (g), while part of the mother liquor is preferably passed to step (d). Due to increased discharge of isomers, the filtrate a concentration level drops in the second crystallization stage, thereby improving the product purity. Dehumidifying filtrates are understood to be those filtrates which are removed from the filter cake as residual washing liquids on applying a vacuum of 5 to 500 mbar.

Another possible way of lowering the isomer concentration in the second crystallization stage, (h), and thereby increasing the resulting product purity involves evaporating 0 or 0.1 to 35 wt-%, preferably 0 or 0.1 to 10 wt-%, of the filtrates obtained in step (i) and/or (O), passing the bisphenol A and isomer-free top product, consisting essentially of phenol, water and optionally acetone, to step (g) and/or step (j), optionally after further purification, and recycling the bottom product, enriched in bisphenol A and isomers, upstream of step (b). This measure affords better control over the phenol balance of the production facility and hence improves operability.

An alternative embodiment of the process comprises the preparation of BPA in two categories of purity, namely a BPA with a purity of 99.5 to 99.75 wt-% and a high-purity BPA with a purity of at least 99.8 wt-%, in the same production facility. In this case, both a one-stage and a two-stage crystallization, as well as the subsequent product work-up (solid-liquid separation, washing, dissolution, and removal of phenol), are carried out separately for the different BPA purities. However, the mother liquors from the first crystallization stage and first solid-liquid separation stage may be processed together and recycled into the reaction. In this case, the product mixture formed in the reaction is subjected to separate crystallization and product work-up for the different BPA purities.

In step (k) phenol from the solid phase obtained in step (j), especially the filter cake, is removed from BPA-phenol adducts by thermal separation at temperatures of at least 120° C. Preferably, the phenol is completely or partially removed by distillative and/or desorptive methods such as those described e.g. in DE 198 48 026 A, DE 198 60 144 A and DE 199 61 566 A, the contents of which are incorporated herein by reference.

The process according to the invention makes it possible to prepare bisphenol A with a purity of at least 99.8 wt-% of p,p-BPA, a low color index and a high temperature stability.

After the phenol has been separated off to levels preferably of max. 600 ppm and particularly preferably of max. 100 ppm in step (k), a bisphenol A melt is obtained which may be used, optionally without prior solidification, for the preparation of polycarbonate by the transesterification process (melt polycarbonate). However, the bisphenol A melt may also be solidified by known processes such as the prilling process, and/or by exfoliation, for sale or further utilization. Furthermore, the melt may be dissolved in a sodium hydroxide solution and used for the preparation of polycarbonate by a phase boundary method or other method.

This gives a polycarbonate with a low yellowness index (YI) of max. 1.5 as a measure of the color.

In another embodiment of the present invention, the melt is evaporated in step (k) to residual phenol contents of 2 to 20 wt-%, as described in DE 199 54 787 A incorporated herein by reference, and this melt, without prior solidification, is reacted with diphenyl carbonate by the melt process to give polycarbonate. This again yields a polycarbonate with a low YI (max 1.5).

The liquid phase obtained from the solid-liquid separation in step (c) and (d) (mother and washing liquor) contains phenol, BPA, water and optionally acetone and co-catalyst, and is enriched in the secondary components typically obtained in the preparation of BPA. The water is preferably separated from the liquid phase obtained in step (c) and (d) (mother and washing liquor) to residual contents of max. 0.3 wt-%, preferably of 0.25 wt-%, and at least 90 wt-% of the resulting solution is advantageously recycled into the reaction in step (a), with the optional addition of acetone, phenol and co-catalyst.

With an increasing concentration level of water and/or optionally acetone in the second crystallization stage, (h), it may be advantageous to carry out a thermal separation of water and/or acetone from the phenolic solution transferred from step (i) and (j) to step (d), and optionally to recycle the resulting distillate into the second crystallization step (in or upstream of step (h)), especially if the concentration of these compounds in the second crystallization stage becomes so high that a separate evaporation or distillation of the solutions transferred from step (i) and (j) to step (d), as a rough separation, offers economic advantages compared with the separation of water in the main circuit. After work-up of the material stream between step (c) and (d) and step (a) in order to remove water, a partial stream of preferably 0.5 to 10 wt-%, or so-called discharge, is taken off. This partial stream is withdrawn from the process chain as so-called BPA resin, optionally after the recovery of phenol, isopropenylphenol, bisphenol A or other components and optionally after prior treatment with acid(s) and/or base(s).

By way of example, the discharge may advantageously be subjected first to rearrangement on an acidic ion exchanger, then to concentration by partial distillation of the phenol, and then to crystallization and filtration. The distillate obtained may be used to wash the filter cake and rinse the cloth. The crop of crystals containing BPA may be recycled into the first crystallization stage, (b), and the isomer-enriched mother liquor may be worked up further, preferably by distillation, to recover more phenol.

EXAMPLES

Example 1a

Embodiment

A product mixture obtained in step (a), containing 70.1 wt-% of phenol, 22.0 wt-% of BPA, 6.6 wt-% of isomers, 1.1 wt-% of water and 0.2 wt-% of acetone, was introduced continuously into a crystallizer for the purpose of suspension crystallization in step (b) (1st crystallization stage). The mean residence time in the crystallizer was 1 h and the mixture was circulated through an external heat exchanger. The temperature of the crystallizer was thus adjusted to 41° C. The crop of crystals found under steady-state conditions had the phenol-free composition shown in Table 1, row 1. A sturdily acicular crystal habit was found.

The crystals of BPA-phenol adduct filtered off step (c) and washed in step (d) were melted and mixed with a phenolic solution in step (g) to form a homogeneous solution containing 77 wt-% of phenol, 22 wt-% of BPA and 1 wt-% of isomers, as shown in Table 1, row 2.

This homogeneous solution shown in Table 1, row 2 was mixed with water in a ratio of 99:1 and crystallized under the conditions described (residence time 1 h, external heat exchanger, temperature 41° C.) (2nd crystallization stage, step (h)). The crystals of BPA-phenol adduct found under steady-state conditions after filtration (i) and washing in step (j) had the phenol-free composition shown in Table 1, row 4. A sturdy, slightly acicular crystal habit was found.

Example 1b

Comparative Example

A product mixture obtained analogously to step (a), containing 70.1 wt-% of phenol, 22.0 wt-% of BPA, 6.6 wt-% of isomers, 1.1 wt-% of water and 0.2 wt-% of acetone, was introduced continuously into a crystallizer for the purpose of suspension crystallization (1st crystallization stage). The mean residence time in the crystallizer was 1 h and the mixture was circulated through an external heat exchanger. The temperature of the crystallizer was thus adjusted to 41° C. The crop of crystals found under steady-stage conditions had the phenol-free composition shown in Table 1, row 1. A clear acicular crystal habit was found.

The filtered and washed crystals of BPA-phenol adduct were melted and mixed with a phenolic solution to form a homogeneous solution containing 77 wt-% of phenol, 22 wt-% of BPA and 1 wt-% of isomers, as shown in Table 1, row 2.

This homogeneous solution was crystallized under the conditions described above (residence time 1 h, external heat exchanger, temperature 41° C.) in a suspension crystallization without the presence of water (2nd crystallization stage). The crystals of BPA-phenol adduct found under steady-state conditions after filtration and washing had the phenol-free composition shown in Table 1, row 3. A distinctly acicular crystal habit was found. The product purity was lower than in Example 1a) according to the invention.

TABLE 1

Purity of the crystals of BPA-phenol adduct without taking the phenol into account, and composition of the recrystallization feed

| | Phenol [wt-%] | p,p-BPA [wt-%] | Isomers [wt-%] |
|---|---|---|---|
| 1. crystallized once | | 99.29 | 0.71 |
| 2. recrystallization feed | 77 | 22 | 1 |
| 3. recrystallized (Comparative Example 1 b)) | | 99.84 | 0.16 |
| 4. recrystallized, addition of water (Embodiment 1 a)) | | 99.88 | 0.12 |

Example 2

A phenolic solution containing 4 wt-% of acetone, max. 0.1 wt-% of water, 9 wt-% of p,p'-BPA and isomers was reacted in step (a) at a rate of 50 t/h in the presence of an ion exchange resin in sulfonic acid form and mercaptopropionic acid as co-catalyst. The reaction product contained about 24 wt-% of p,p'-BPA.

After the addition of a partial stream enriched in p,p'-BPA from steps (c) and (d) and (i) and (j), BPA-phenol adduct was crystallized continuously from the resulting mixture in a first crystallization stage, (b), in two steps at 54° C. and 41° C. with a total residence time of 8 h, the suspension being cooled and the heat of crystallization dissipated by means of heat exchangers.

The solid-liquid separation of the suspension in step (c) was carried out on a vacuum rotary filter, the resulting filter cake as well being washed with a phenolic solution at about 55° C. in step (d).

The filter cake was first melted and then mixed with a phenolic solution to give a homogeneous solution in step (g). The solution prepared in this way contained 25 wt-% of p,p'-BPA and 0.3 wt-% of isomers. Water was added before crystallization to give a water content of 1 wt-% in the homogeneous solution. The temperature of the solution was adjusted to 79° C.

The repeat crystallization in step (h) was carried out continuously in two steps at 54° C. and 41° C., the suspension being cooled and the heat of crystallization dissipated by means of heat exchangers in each case. The residence time in this crystallization stage (h) was 4 h.

In step (i) the suspension was filtered on a vacuum rotary filter and washed (j) at about 55° C. with a phenolic solution containing max. 0.1 wt-% of isomers.

The resulting crystals of BPA-phenol adduct moistened with phenol, having a residual moisture content of about 25 wt-%, were then melted and the phenol was removed by thermal separation in step (k) to a content of 90 ppm. After prilling of the BPA melt, the BPA obtained had a purity of at least 99.9% and a color index of less than 20 Hazen units.

The mother liquor from steps (c) and (d) and (i) and (j) was extensively dewatered. A partial stream was taken from the dewatered mother liquor and subjected to distillation of the part of the phenol. The distillate was used to wash the filter cake and rinse the cloth. After further separation by means of crystallization and filtration, a BPA-containing stream from the BPA-enriched bottom product was recycled into the first crystallization stage, (b), and the isomer-enriched mother liquor was worked up further to recover phenol.

Example 3

Simulation of a Two-Stage Crystallization Process

A simulation study of a two-stage crystallization process for the preparation of high-purity bisphenol A is described below. The simulations were performed using the commercial software package Aspen Custom Modeler®. The software is based on a process model with special models for the reaction (detailed reaction kinetics), for the kinetics of the incorporation of impurities in the crystallization, and for other basic operations.

Step (a): Reaction of acetone and phenol to give p,p'-BPA and isomers, with the formation of water, in adiabatic fixed bed reactors in the presence of a co-catalyst under the following inflow conditions:

4 wt-% of acetone, 0.07 wt-% of water, 9 wt-% of p,p'-BPA; temperature: 52° C.

Step (b): The reaction products, containing 22.5 wt-% of p,p'-BPA, were passed to the first crystallization stage, where BPA-phenol adduct was crystallized in two steps at 54° C. and 41° C. with a total residence time of 5 h. The calculated purity of the crystals was 99.68 wt-%, based on bisphenol A.

Step (c): The suspension was filtered through a vacuum rotary filter,

Step (d): washed and dehumidified on the same vacuum rotary filter. The filter cake was washed using a partial stream of 27% of the filtrates from step (i) and (j), corresponding to a ratio of amount of washing liquid to amount of resulting solid of 0.9.

The phenolic mother liquor discharged from the recrystallization stage contained 9 wt-% of p,p'-BPA, 0.3 wt-% of isomers and 1.3 wt-% of water. Some of this partial stream was used together with recycled phenols from the plant to clean the filter cloth.

The dehumidified filter cake had a residual moisture content of 25 wt-%. With the impurities from the mother liquor still adhering to the crystals, and from the isomer-laden washing liquid, the purity of the filter cake after leaving the rotary filter was 99.4 wt-%, based on p,p'-BPA.

Step (g): The filter cake from (d) was melted and mixed with the residual filtrates from (i) and (j) so that the concentration of p,p'-BPA in the inflow of the second crystallization stage, (h), was 23 wt-%. The solution formed also contained 0.3 wt-% of isomers and 1 wt-% of water.

Step (h): Crystallization in two steps at 54° C./41° C. with a total residence time of 5.5 h. The calculated purity of the adduct crystals was 99.93 wt-%, based on p,p'-BPA.

Step (i): The suspension obtained was filtered

Step (j): washed with fresh phenol and recycled phenol streams from the plant, and then dehumidified. Part of these phenol streams used in step (j) for washing was also used to clean the filter cloth. The amount of washing liquid used to wash the filter (j) cake was 71 wt-%, based on the solid obtained. The filtrates obtained from filtration and washing in step (i) and (j) were combined and recycled into steps (d) and (g) together with the filter cloth clearing liquor.

Step (k): The filter cake, with a residual moisture content of 25 wt-%, was melted. The phenol content was reduced by means of thermal separation to a residual value of 150 ppm in the BPA melt. The resulting phenol was passed to step (j). The BPA melt obtained had a purity of 99.92 wt-%, based on p,p'-BPA.

The mother and washing liquor from step (c) and (d) was dewatered to a water content of 0.075 wt-%. A partial stream thereof, corresponding to 4% of the total amount, was taken off in order to discharge the isomers as BPA resin after downstream recovery of the phenol. The remaining part of the dewatered mother liquor was recycled into the reaction in step (a), with the addition of acetone, phenol and a co-catalyst.

According to the simulation study, the impurity content of the product decreased by 12% if the filtrates from filtration and washing in step (i) and (j) were not combined but separated in such a way that the mother liquor more heavily laden with isomers (filtrate from the filtration (i)) was preferably passed to step (d) and the washing filtrates from (j) were preferably passed to step (g).

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

All documents referred to herein are specifically incorporated herein by reference in their entireties.

As used herein and in the following claims, articles such as "the", "a" and "an" can connote the singular or plural.

What is claimed is:

1. A process for the preparation of bisphenol A comprising:
   a) reacting phenol with acetone in the presence of an acidic ion exchanger and a sulfur-containing co-catalyst to produce a product mixture comprising bisphenol A, phenol, BPA isomers, un-reacted acetone, and water, wherein the resulting product mixture is not subjected to distillation upstream of steps (b) or (c) to remove readily volatile constituents including water;
   b) continuously obtaining from the product mixture crystals of bisphenol A-phenol adduct by suspension crystallization in at least one crystallizer provided with at least one heat exchanger, said product mixture containing 0.1 to 6% by weight of water;
   c) separating the adduct obtained in (b) by a first solid-liquid separation to obtain a first solid phase and a first liquid phase;
   d) washing the first solid phase with a solution comprising phenol to obtain a washed solid phase and a second liquid phase;
   e) distilling the first liquid phase and said second liquid phase to obtain a dewatered solution comprising 5 to 15 wt.-% p,p-BPA, 3 to 12 wt.-% isomers of BPA and less than 0.3 wt.-% water, the percentages based on the weight of the dewatered solution;
   f) optionally introducing at least 90 wt.-% by weight of the dewatered solution into (a);
   g) adding phenol and water to the washed solid phase obtained in (d) to obtain a homogeneous material system comprising 15 to 35 wt.-% p,p'-BPA, 0.05 to 2 wt.-% isomers of BPA and 0.1 to 10 wt.-% water;
   h) continuously obtaining from the homogeneous material system crystals of bisphenol A-phenol adduct by suspension crystallization in at least one crystallizer provided with at least one heat exchanger;
   i) separating the crystals obtained in (h) by a second solid-liquid separation to obtain a second solid phase;
   j) washing the second solid phase with a solution comprising phenol to obtain a washed adduct; and
   k) optionally heating the washed adduct to at least 120° C. to at least potentially remove phenol.

2. A process according to claim 1, wherein 50 to 90 wt.-%, of a liquid phase obtained in (i) and (j) is used in (g).

3. A process according to claim 1, wherein 10 to 50 wt.-%, of a liquid phase obtained in (i) and (j) is recycled into (d) for washing.

4. A process according to claim 1, wherein the solution comprising phenol in (j) comprises not more than 1.0% by weight of isopropenylphenol BPA and isomers thereof, and any secondary components.

5. A process according to claim 1, wherein the washed solid phase obtained in (d) is first melted before phenol is added in (g).

6. A process according to claim 1, wherein at least one of said first and/or second solid-liquid separation is carried out in a vacuum rotary filter.

7. A process according to claim 1, wherein the solution comprising phenol of (d) comprises 84 to 99.45 wt.-% phenol, 0.5 to 15 wt.-% BPA and 0.05 to 1.0 wt.-% BPA isomers, the percentages based on the weight of all components of the solution except water.

8. A process according to claim 1, wherein the solution comprising phenol of (d) comprises 0.05 to 12 wt.-% water, the percentage based on the total weight of said solution.

9. A process according to claim 1, wherein 5 to 100 wt.-% of the solution comprising phenol of (d) originates from (i) and (j).

10. A process according to claim 1, wherein the crystallization of (b), is carried out in two steps in series at temperatures that differ one from the other, and wherein the crystallization of (h) is carried out in one step in at least two crystallizers operating in parallel.

11. A process according to claim 1, wherein the material system of (g) comprises at most 5 wt.-% acetone, the percentage based on the weight of the system.

12. A process according to claim 1, wherein at least part of a liquid phase from the solid-liquid separation of (i) and at least part of a liquid phase from washing in (j) are collected separately, at least part of the liquid phase from the solid-liquid separation of (i) is recycled into (d) and/or at least part of the liquid phase from the washing is recycled into (g).

13. A process according to claim 1, wherein 0 to 35 wt.-%, of liquid phases obtained in (i) and/or (j) is evaporated, such that a top product is passed to (d) and/or (f) and a bottom product is recycled upstream of (b).

14. A process for the preparation of bisphenol A comprising:
   a) reacting phenol with acetone in the presence of an acidic ion exchanger and a sulfur-containing co-catalyst to produce a product mixture comprising bisphenol A, phenol, BPA isomers, un-reacted acetone, and water, wherein the resulting product mixture is not subjected to distillation upstream of steps (b) or (c) to remove readily volatile constituents including water;
   b) continuously obtaining from the product mixture crystals of bisphenol A-phenol adduct by suspension crystallization in at least one crystallizer provided with at least one heat exchanger, said product mixture containing 0.1 to 6% by weight of water;
   c) separating the adduct obtained in (b) by a first solid-liquid separation to obtain a first solid phase and a first liquid phase;
   d) washing the first solid phase with a solution comprising phenol to obtain a washed solid phase and a second liquid phase;
   e) distilling the first liquid phase and said second liquid phase to obtain a dewatered solution comprising less than 0.3 wt.-% water, the percentages based on the weight of the dewatered solution;
   f) optionally introducing at least a portion of the dewatered solution into (a);
   g) adding phenol and water to the washed solid phase obtained in (d) to obtain a homogeneous material system comprising 15 to 35 wt.-% p,p'-BPA, 0.05 to 2 wt.-% isomers of BPA and 0.1 to 10 wt.-% water;
   h) continuously obtaining from the homogeneous material system crystals of bisphenol A-phenol adduct by suspension crystallization in at least one crystallizer provided with at least one heat exchanger;
   i) separating the crystals obtained in (h) by a second solid-liquid separation to obtain a second solid phase;
   j) washing the second solid phase with a solution comprising phenol to obtain a washed adduct; and
   k) optionally heating the washed adduct to at least 120° C. to at least partially remove phenol.

* * * * *